(12) United States Patent
Ingole et al.

(10) Patent No.: US 10,138,082 B2
(45) Date of Patent: Nov. 27, 2018

(54) APPARATUS AND METHOD FOR MECHANICALLY GRIPPING AND TRANSPORTING WEBS OF MATERIAL

(71) Applicant: Curt G. Joa, Inc., Sheboygan Falls, WI (US)

(72) Inventors: Sudeep Ingole, Sheboygan, WI (US); Lloyd Kreif, Sheboygan Falls, WI (US); Brenden Schulz, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 15/140,983

(22) Filed: Apr. 28, 2016

(65) Prior Publication Data

US 2016/0318727 A1 Nov. 3, 2016

Related U.S. Application Data

(60) Provisional application No. 62/155,935, filed on May 1, 2015.

(51) Int. Cl.
*B65H 5/12* (2006.01)
*A61F 13/15* (2006.01)
(Continued)

(52) U.S. Cl.
CPC ......... *B65H 5/12* (2013.01); *A61F 13/15764* (2013.01); *B65H 29/048* (2013.01);
(Continued)

(58) Field of Classification Search
CPC . B65H 5/12; B65H 5/08; B65H 5/021; B65H 29/003; B65H 29/02; B65H 29/04; B65H 29/045; B65H 29/048; B65H 29/06; B65H 29/08; B65H 2301/4471; B65H 2301/44712; B65H 2301/44714;
(Continued)

(56) References Cited

U.S. PATENT DOCUMENTS 3,862,610 A 1/1975 Brocklehurst
4,525,317 A 6/1985 Okada et al.
(Continued)

FOREIGN PATENT DOCUMENTS

| DE | 102005033070 A1 | 1/2007 | |
|---|---|---|---|
| FR | 2759994 A1 * | 8/1998 | ............. B65H 15/00 |
| SU | 1659343 A * | 6/1991 | ............... B65H 3/08 |

OTHER PUBLICATIONS

International Search Report pertaining to PCT/US2016/029736, dated Jul. 27, 2016, 8 pages.

*Primary Examiner* — Michael C McCullough
(74) *Attorney, Agent, or Firm* — Ryan Kromholz & Manion, S.C.

(57) ABSTRACT

Individual fibers of a material layer are pinched within adjacent coils of a spring in the present invention by a spring-like surface carried by a moving object such as a conveyor belt, rotating drum or rotating puck. The spring coils are slightly opened to accept the individual fibers. Next the spring coils are closed to carry and transport the web of fibers. At a deposition point, the coil springs, carried by a moving object such as a conveyor belt, rotating drum or rotating puck, are opened slightly, releasing fibers and depositing the web at a desired location.

5 Claims, 5 Drawing Sheets

(51) Int. Cl.
*B65H 29/04* (2006.01)
*B65H 39/14* (2006.01)

(52) U.S. Cl.
CPC ......... *B65H 39/14* (2013.01); *B65H 2301/23* (2013.01); *B65H 2301/44338* (2013.01); *B65H 2301/44712* (2013.01); *B65H 2405/50* (2013.01); *B65H 2801/57* (2013.01)

(58) Field of Classification Search
CPC ........... B65H 2301/44716; B65H 2301/44718; B65H 2405/50; B65H 2405/57; B65H 2405/571; B65H 2402/20; B65H 2402/22
USPC .......................... 198/867.06, 867.1, 803.13
See application file for complete search history.

(56) References Cited

U.S. PATENT DOCUMENTS

| | | | | |
|---|---|---|---|---|
| 4,779,717 A | * | 10/1988 | Eberle | B65H 29/003 101/408 |
| 4,782,988 A | * | 11/1988 | Nishiyama | A44B 18/0069 226/190 |
| 4,799,664 A | * | 1/1989 | Burger | B65H 5/085 271/204 |
| 5,025,910 A | | 6/1991 | Lasure et al. | |
| 6,478,297 B1 | * | 11/2002 | Messerschmid | B65H 5/085 198/803.1 |
| 6,861,380 B2 | * | 3/2005 | Garnier | D21H 27/38 442/327 |
| 2011/0088233 A1 | | 4/2011 | McCabe et al. | |
| 2013/0312234 A1 | | 11/2013 | Riesinger | |

* cited by examiner

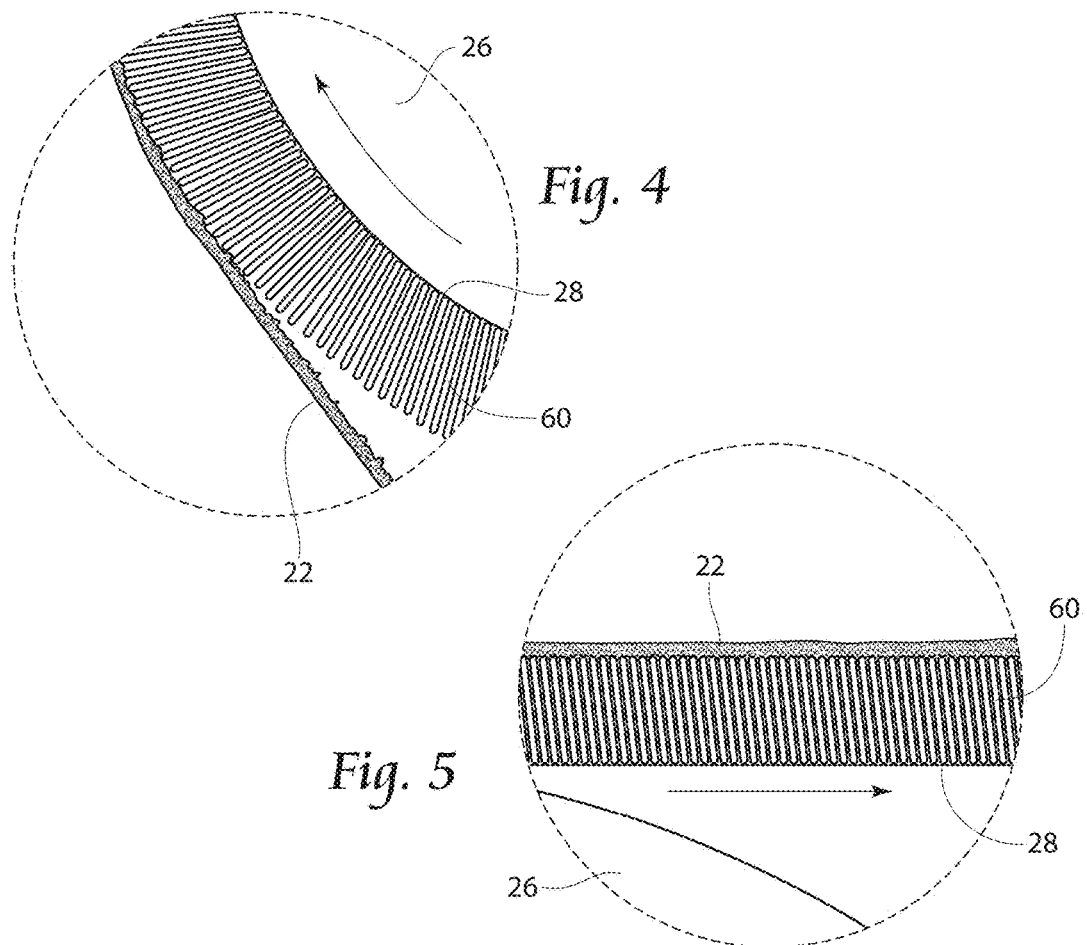
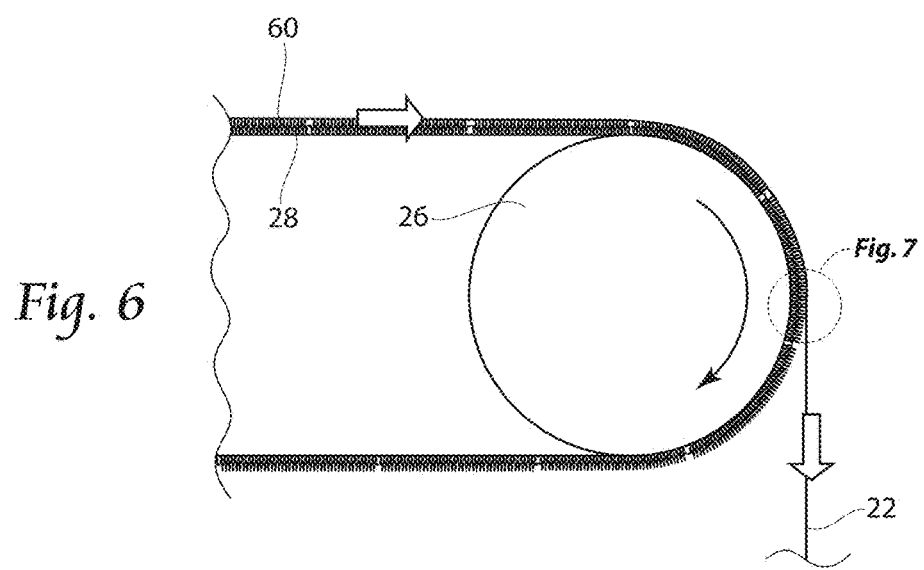

APPARATUS AND METHOD FOR MECHANICALLY GRIPPING AND TRANSPORTING WEBS OF MATERIAL

RELATED APPLICATION

This application claims the benefit of U.S. Provisional Patent Application Ser. No. 62/155,935, filed 1 May 2015.

BACKGROUND OF THE INVENTION

The present invention relates to disposable hygiene products and more specifically, to methods and apparatuses for processing disposable hygiene products such as baby diapers, adult diapers, disposable undergarments, incontinence devices, sanitary napkins and the like.

More specifically, the invention relates to mechanically gripping traveling webs of material to reduce reliance on vacuum. Vacuum is used in many parts of a diaper manufacturing process. For instance, during pulp core formation, vacuum draws pulp fibers into forming pockets on a core forming drum. Vacuum can also be used in vacuum conveyors.

Typical vacuum rolls used in the prior art have; rows of vacuum holes which are fed by cross-drilled ports, each being exposed to the source of vacuum by commutations, as the ports move into a zone of negative pressure in a stationary manifold. Such a configuration serves to apply vacuum sequentially to each successive row of holes.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator-collects a substantial length of the first web. By using an accumulator, the material being fed into the process can continue, yet the trailing end of the material can be stopped or slowed for a short time; interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

Generally, diapers comprise an absorbent insert or patch and a chassis, which, when the diaper is worn, supports the insert proximate a wearer's body. Additionally, diapers may include: other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

Continual improvements and competitive pressures have incrementally increased the operational speeds of disposable diaper converters. As speeds increased, the mechanical integrity and operational capabilities of the applicators had to be improved accordingly. The prior art is quite successful when processing full-width or symmetrical webs using vacuum, and vacuum is nearly universally used in diaper production. However, as speeds have increased in manufacturing, so too has vacuum demand. Along with significant increase in vacuum demand comes the expense of powering convention vacuum forming techniques, and the noise associated with traditional vacuum pumps.

It is therefore an object of this invention to provide an apparatus which can minimize reliance on vacuum to transport and control material webs during the disposable product manufacturing process where control and transport of material webs.

SUMMARY OF THE INVENTION

The present invention provides a method and apparatus for mechanically securing portions of textured surfaces of a traveling web of material.

Disposable products often are made of a variety of materials such as woven and nonwoven materials. These fabric-like materials are formed by many interlinked long fibers which are bonded together. During the disposable product manufacturing process, these fabrics are placed into the system at different times and places, depending on the diaper construction desired.

The woven and nonwoven materials are smooth to the touch, but when viewed microscopically, individual fibers are linked together such that individual fibers stick up from the relatively smooth surface. The pinching effect between two adjacent spring segments is utilized to hold the nonwoven textured surface. Similar effect can be generated by micro-grips that utilize similar mechanism as in springs. The individual fibers of a material layer are pinched within adjacent coils of a spring or alternate mechanism in the present invention by a spring-like surface carried by a moving object such as a conveyor belt, rotating drum or rotating puck. There are naturally some fibers that stick up and they are good candidates to be grabbed by openings within a closing spring or similar mechanism. Additional aspects of the present invention is to either mechanically (for example using compliance materials or vacuum), chemically, or electrostatically encourage fibers to "stand up" or disrupt the individual fibers of a material in advance of a spring-gripping step.

Adjacent coil springs of the present invention are slightly opened, for example as the coil springs travel around a rounded corner, to allow fibers from a material web to enter the void space between the opened coil springs. The coil springs next closing upon exiting the end of a diameter to positively grasp individual fibers between coil springs, and the coil springs coil springs remain closed while the spring travels. The coil springs then are themselves carried by a conveyor, as they engage the fibers as the spring travels around a corner opening the coils, travel and transport the material web, and then release the material web. At a desired release point, coil springs are again slightly opened (for instance as the coil springs travel around a corner or are stretched), allowing the fibers to escape the grasp of the adjacent coil springs.

For non-linear travel such as a rotating puck, the springs can be oriented to maintain the closed coil condition along a curved surface. For instance, an active puck, can carry springs, and the puck surface shape can change before material pickup (radius), during material pickup and transport (radius to straight), and finally to release; material at drop-off point (straight to radius).

This spring gripping technique can be used with endless-belt conveyors, as coil springs can be integrated with a conveyor belt.

An apparatus for transporting material is disclosed, the apparatus comprising a series of biased gripping members, said biased gripping members operable between an open position and a closed position, said biased gripping members transported in a web processing system from an acquisition point for receiving material, to a transport segment for moving said material, to a deposition point for releasing said material, said biased gripping members in said open position at said acquisition point and receiving a portion of said material between adjacent biased gripping members, said biased gripping members in said closed position at said transport segment, and retaining said portion of said material between adjacent biased gripping members, said biased gripping members in said open position at said deposition point and releasing said portion of said material between adjacent biased gripping members.

The apparatus further comprises a rotating body carrying said series of biased gripping members, and the rotating body can be either a belt or a drum or a puck. The apparatus can be used to transport either continuous web of material, such as a fibrous non-woven, or a discrete piece of material.

BRIEF DESCRIPTION OF THE DRAWINGS

FIG. 4 is a side close up view of coil spring conveyor of the present invention, with the coil springs traveling about a radius and adjacent coil springs opening slightly to accept individual fibers of a traveling web;

FIG. 5 is a side close up view of coil spring conveyor of the present invention, with the coil springs traveling linearly and adjacent coil springs closed to retain and transport individual fibers of a traveling web;

FIGS. 6 and 7 are a side and side close up view, respectively, of coil spring conveyor of the present invention, with the coil springs traveling about a radius and adjacent coil springs opening slightly to disengage and release individual fibers of a traveling web;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
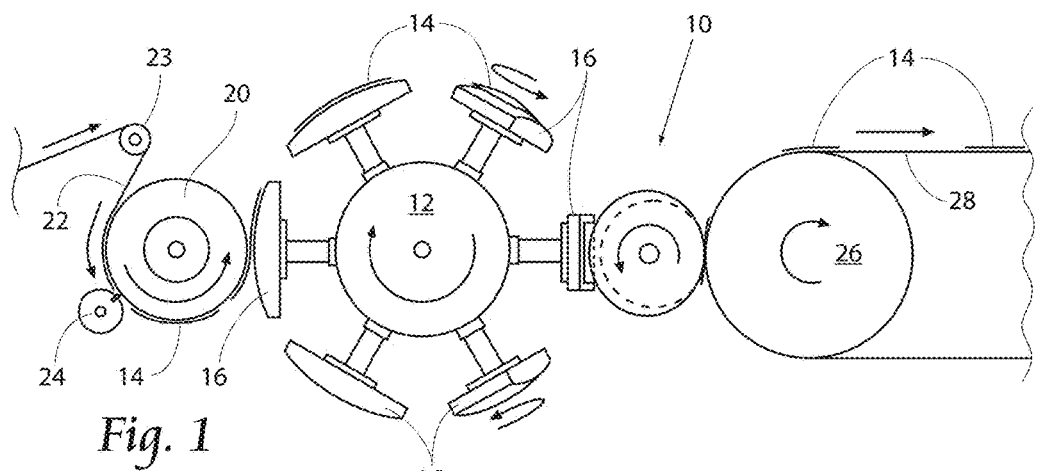
FIG. 1 is a side; view of a portion of a disposable product manufacturing unit of the prior art, showing rotary and linear conveyance.

Referring now FIG. 1, a side view of a portion of a disposable product manufacturing unit of the prior art is shown. An apparatus 10 carrying pucks, or transfer heads 16, is adapted to receive a series of articles 14 from an upstream conveyor or vacuum drum, but in one embodiment the discrete articles have been severed from a web 22 by a slip cut unit 23/24 which is used to process a discrete web 22 into individual pieces 14. Pieces 14 are carried by drum 20 onto a pad turning device 12 which includes a plurality of radially extending transfer heads 16, which deposit the pieces 14 onto drum 26 which rotates an endless conveyor 28.

The location where articles 14 are received from the upstream point onto the pucks 16 is known as the pick up point. The location where articles 14 are deposited from the pucks 16 to a downstream drum or conveyor 26/28 is known as the lay down point.

The pad turning device 12 may be, for example, a rotary pad turner of the type more fully described in U.S. Pat. No. 5,025,910 which is incorporated herein by reference. The articles 14, such as absorbent pads, may be any elongated articles which need to be rotated approximately 90° during the course of a manufacturing operation. In the present invention, the elongated articles are also stretched away from their center point in a direction, such as a radial direction, away from the axis of the puck 16 as will be described later.

Such pad turning devices 12 are especially needed and are suited for use in connection with the manufacture and packaging of sanitary napkins as well as absorbent pads which are used in the assembly of disposable garments such as adult incontinence garments or children's training pants.

Also seen in FIG. 1, articles 14 are successively and individually picked-up by the transfer heads 16 of the pad transfer device 12. In the illustrated embodiment, the articles 14 are picked up from a vacuum drum (not shown).

A conveyor 28 or the like transports the articles 14 for further processing or to a packaging device, as required by a particular application. Both linear (by belt 28) and rotary (by drums such as drum 20 or pad transfer device 12) conveyance is shown in the unit of FIG. 1, both instances in which the present invention can be used.

Figure 2:
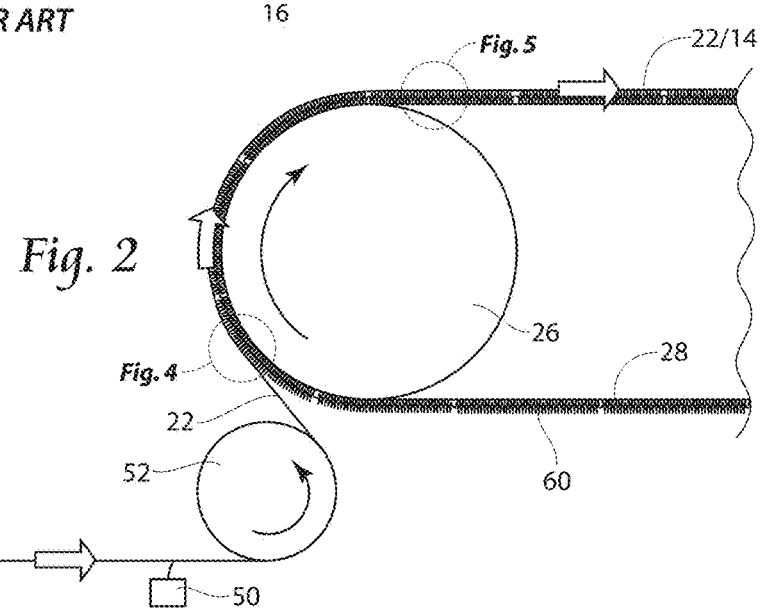
FIG. 2 is a side view of a spring gripping technique can be used with an endless-belt conveyors, with coil springs integrated with a conveyor belt, the coil springs opening slightly as they travel around a radius to accept individual fibers, and then closing upon exit of the radius to maintain the individual fibers.

Referring now FIG. 2, a side view of a spring gripping apparatus and technique is shown. Web 22 optionally passes a web disruption unit 50, which can either mechanically, chemically, or electrostatically encourage individual fibers of web 22 to "stand up" or disrupt the individual fibers of a material in advance of a spring-gripping step. As the web 22 continues, the web 22 is introduced to a coil spring series 60, which is carried by endless-belt conveyor 28, which is in turn rotated by drum 26. As individual coil springs 60 of the coil spring series 60 carried by conveyor belt 28 travel around a radius of drum 26, the coil springs 60 open slightly. The coil springs 60 accept individual fibers of web 22 as is best shown in FIG. 4. The coil springs 60 then close upon exit of the radius of drum 26 to maintain the individual fibers of web 22, as best shown in FIG. 5.

Figure 3:
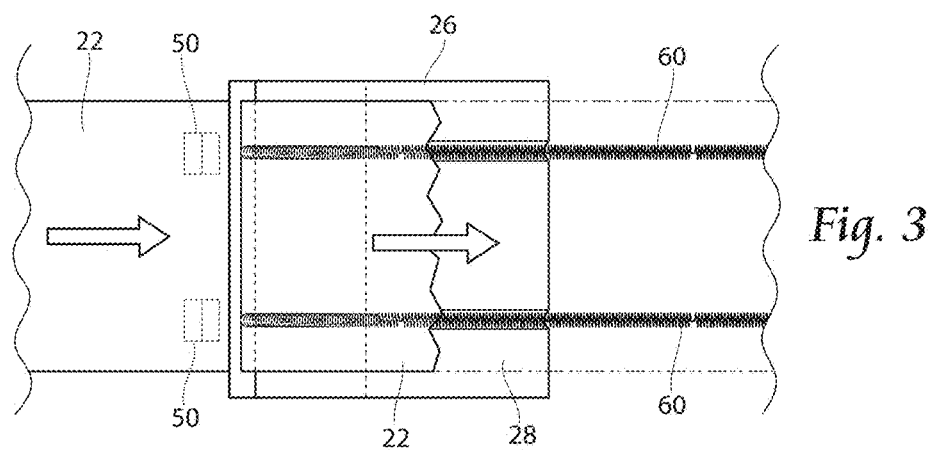
FIG. 3 is a top view of a coil spring conveyor of the present invention.

In a preferred embodiment, as shown in FIG. 3, two series of coil spring series 60 are carried by endless conveyor 28, and corresponding web disruption units 50 are provided upstream of the series of coil spring series 60. It is noted that the present invention contemplates forming or molding spring-like elements directly into a conveyor belt surface as well. Instead of an actual spring, or other geometries that provide a similar spring-like pinching effect can also be incorporated into carrying surfaces such as pucks or conveyor belts as well. For instance, micro-gripping structures can be incorporated directly into belts or pucks to provide an active or passive spring-like gripping surface.

Figure 7:
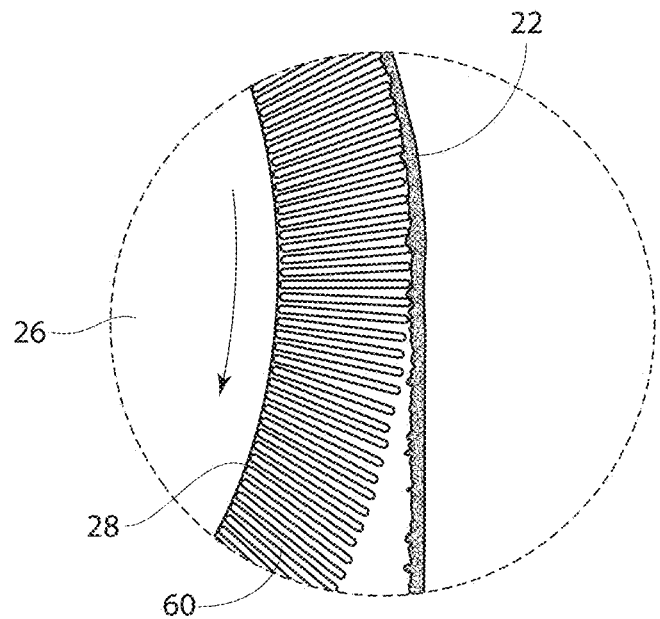
Figure 8:
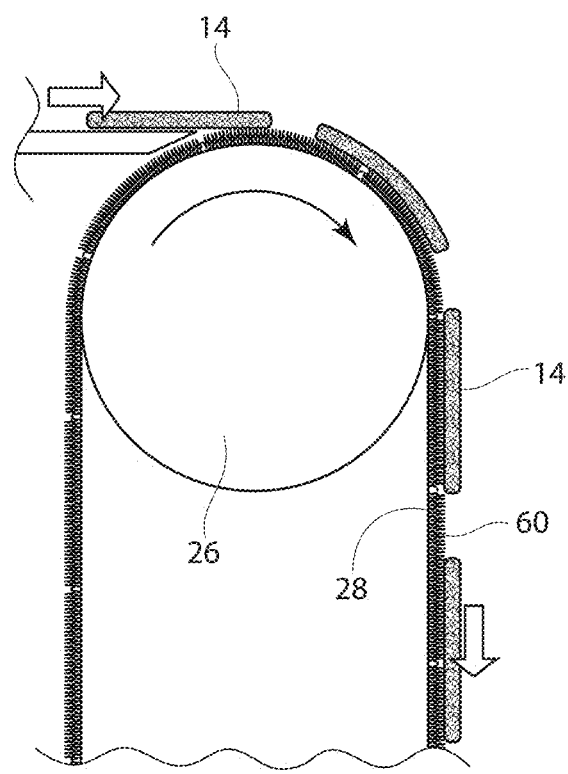
FIG. 8 is a side view of a representative web processing system, with individual fibrous discrete articles approaching a coil spring conveyor of the present invention, with the coil springs traveling about a radius and adjacent coil springs opening slightly to accept individual fibers of a traveling web, and the discrete articles being carried downstream by the conveyor.

Referring to FIGS. 6 and 7, coil series 60 carried by conveyor 28 then travel around an outbound radius of another drum 26. The coil springs 60 travel about a radius of drum and adjacent coil springs opening slightly to disengage and release individual fibers of a traveling web 22. The same pickup and release techniques can be used for linear or curved travel, and can be used to carry continuous webs 22 or discrete pieces 14, as is shown in FIG. 8.

Figure 9:
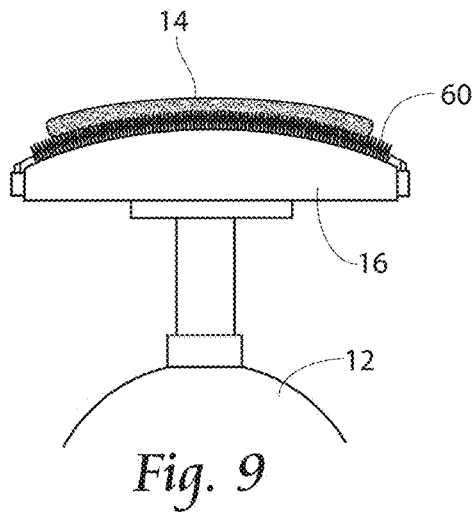
FIGS. 9 and 10 are side views of a coil spring series of the present invention, with the coil springs carried by a rotating puck, the springs oriented and controlled to maintain the closed coil condition along a curved surface.
Figure 10:
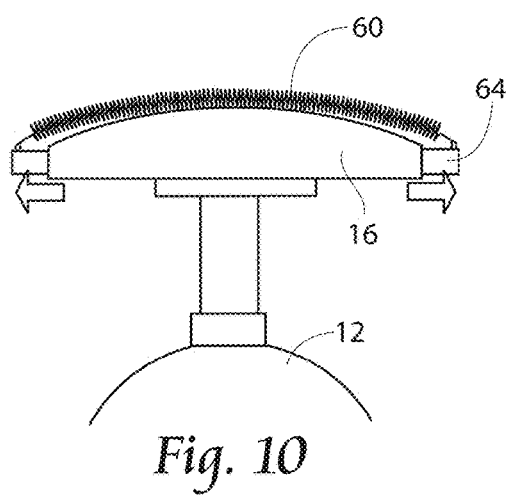
Figure 11:
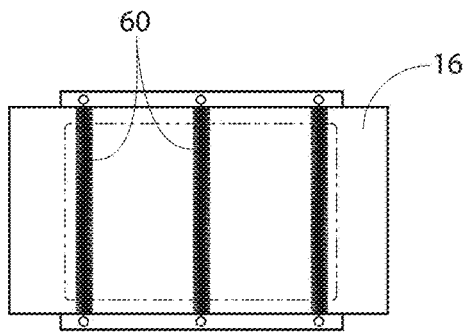
FIGS. 11 and 12 are top views of the embodiment shown in FIGS. 9 and 10, respectively.
Figure 12:
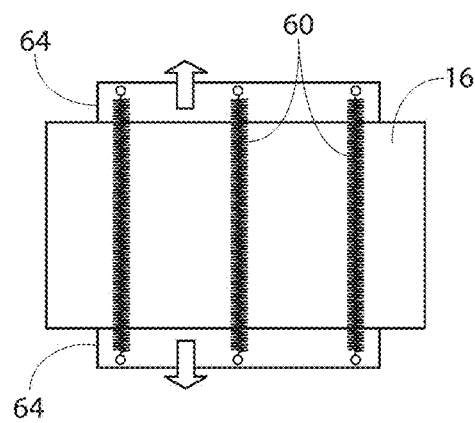

Referring now to FIGS. 9 and 10, side views are shown of a coil spring series 60 of the present invention is shown, with the coil springs 60 carried by a rotating puck 16. The coil spring series 60, of which there may be one or more per puck 16 as shown in FIGS. 11 and 12, carry articles 14. The coil spring series can be stretched by an active unit 64 carried by the puck 16, or the puck 16 itself may be capable of changing surface shape. This action causes the spring 60 to be able to expand, in order to allow individual fibers of a web or discrete piece 14 to enter the spring array, and to contract, in order to maintain and grasp individual fibers of the carried fabric. To release the individual articles 14, the coil spring series 60 can again be stretched to allow the fibers of the articles 14 to escape the grasp of adjacent springs of the series 60.

Figure 13:
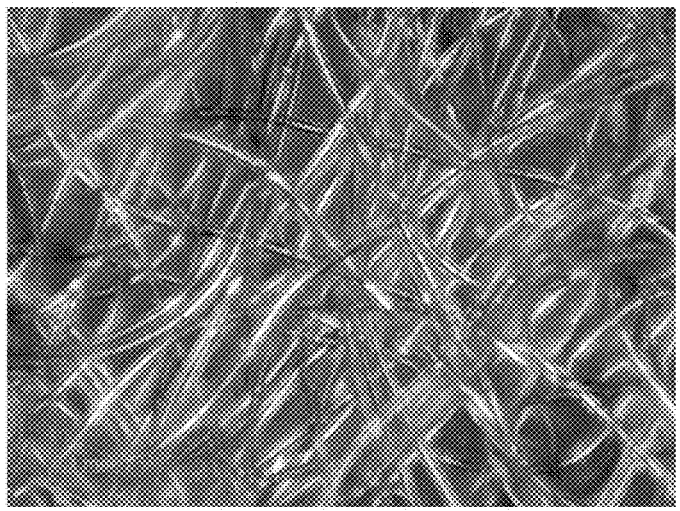
FIGS. 13-15 are microscopic views of non-woven material depicting individual fiber candidates for gripping by spring-like pinching members.
Figure 14:
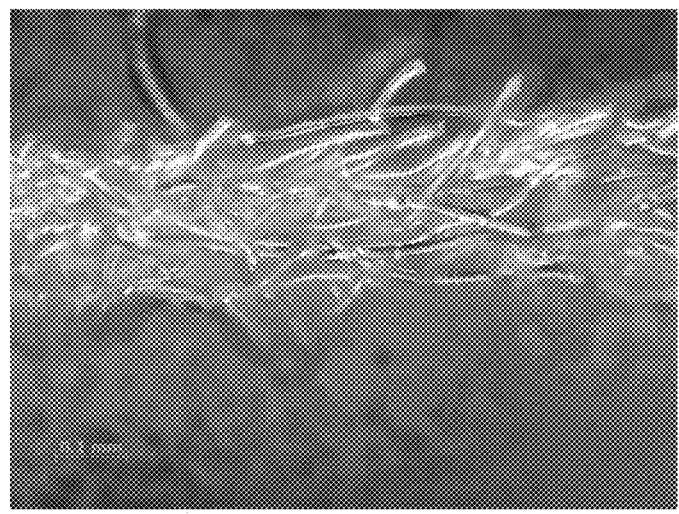
Figure 15:
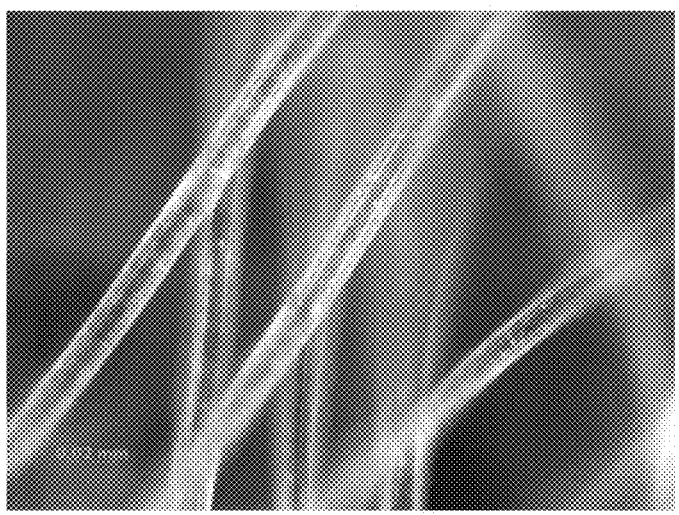

Referring now to FIGS. 13-15, microscopic views of non-woven material depicting individual fiber candidates for gripping by spring-like pinching members are shown. In FIG. 13, a tangled web of microscopic fiber structures present candidates towards a surface of the macroscopic material for which springs or other gripping structures to grab. In cross section, as seen in FIG. 14, it is seen that both loose fiber ends, as well as individual laid down fibers near a surface of the macroscopic material present targets for gripping structures. Similarly, in the microscopic view shown in FIG. 15, spacing between individual fibers at a surface of the non-woven material presents an area around which the gripping structures can operate to close in on, or grab the individual fibers.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An apparatus for transporting material, the apparatus comprising:
    a series of biased gripping members, said biased gripping members operable between an open position and a closed position;
    said biased gripping members transported in a web processing system from an acquisition point for receiving said material, to a transport segment for moving substantially the entire length of said material by gripping substantially the entire length of said material with said gripping members, to a deposition point for releasing said material;
    wherein said biased gripping members are in said open position at said acquisition point and receiving a portion of said material between adjacent biased gripping members; and
    wherein said biased gripping members are in said closed position at said transport segment, and retaining said portion of said material between adjacent biased gripping members; and
    wherein said biased gripping members are in said open position at said deposition point and releasing said portion of said material between adjacent biased gripping members; and a belt carrying said series of biased gripping members.

2. An apparatus according to claim 1, said material comprising a discrete piece of material.

3. An apparatus according to claim 1, said belt rotated about a first drum to open said biased gripping members at said acquisition point and close said biased gripping members past said acquisition point in a downstream machine direction.

4. An apparatus according to claim 3, belt rotated about a second drum to open said biased gripping members at said deposition point.

5. An apparatus according to claim 1, said apparatus further comprising a web disruption unit positioned upstream in a machine direction from said acquisition point, said web disruption unit acting upon said material to disrupt a plurality of fibers of said material.

* * * * *